(12) United States Patent
Toi et al.

(10) Patent No.: US 7,101,511 B2
(45) Date of Patent: Sep. 5, 2006

(54) MICROPLATE LIQUID HANDLING SYSTEM

(75) Inventors: Hiroatsu Toi, Hitachinaka (JP); Kenji Yamada, Hitachinaka (JP); Tadashi Ohkawara, Hitachinaka (JP); Masashi Nagaoka, Hitachinaka (JP)

(73) Assignee: Hitachi Koki Co., Ltd., Tokyo (JP)

( * ) Notice: Subject to any disclaimer, the term of this patent is extended or adjusted under 35 U.S.C. 154(b) by 186 days.

(21) Appl. No.: 10/669,796

(22) Filed: Sep. 25, 2003

(65) Prior Publication Data

US 2004/0094575 A1     May 20, 2004

(30) Foreign Application Priority Data

Nov. 15, 2002 (JP) ............................ P2002-332817

(51) Int. Cl.
*B01L 3/02*     (2006.01)

(52) U.S. Cl. .................................... 422/100; 73/863.32
(58) Field of Classification Search ................ 422/100, 422/102; 73/863.32
See application file for complete search history.

(56) References Cited

U.S. PATENT DOCUMENTS

| | | | | |
|---|---|---|---|---|
| 5,055,263 A | * | 10/1991 | Meltzer | ........................ 422/65 |
| 5,443,791 A | * | 8/1995 | Cathcart et al. | ............... 422/65 |
| 5,714,127 A | * | 2/1998 | DeWitt et al. | ............... 422/131 |
| 6,006,800 A | * | 12/1999 | Nakano | ....................... 141/130 |
| 6,207,031 B1 | | 3/2001 | Adourian et al. | |
| 2001/0048899 A1 | * | 12/2001 | Marouiss et al. | ............ 422/100 |
| 2002/0176801 A1 | * | 11/2002 | Giebeler et al. | ......... 422/82.05 |

FOREIGN PATENT DOCUMENTS

| | | |
|---|---|---|
| DE | 100 08 003 | 8/2001 |
| DE | 103 51 407.4 | 12/2005 |
| JP | 5-232124 | 9/1993 |
| JP | 8-271528 | 10/1996 |
| JP | 2000-83650 | 3/2000 |
| WO | WO 02/49761 | 6/2002 |

* cited by examiner

*Primary Examiner*—Jill Warden
(74) *Attorney, Agent, or Firm*—McGuireWoods LLP

(57) ABSTRACT

A microplate liquid handling system capable of automatically performing both longitudinal collective suction/discharge and lateral collective suction/discharge on a single microplate. The microplate liquid handling system has a main body equipped with a moving device, a rotating mechanism, a dispensing mechanism, and a stage. Connected to the moving device is the dispensing mechanism for performing dispensing on wells in a microplate on the stage through the rotating mechanism. A plurality of cylinders are arranged in a row in the dispensing mechanism. The dispensing mechanism is capable of moving forwards and backwards and to the right and left with respect to the main body, and is rotatable about a vertically directed rotation axis, making it possible to change the direction of the cylinder array from origin position to 90 degrees position and vice versa.

9 Claims, 6 Drawing Sheets

MICROPLATE LIQUID HANDLING SYSTEM

BACKGROUND OF THE INVENTION

1. Field of the Invention

The present invention relates to a microplate liquid handling system and, more particularly, to a microplate liquid handling system for simultaneously delivering liquid reagent, liquid specimen, etc. to a plurality of desired wells for specimen/reagent reaction arranged in a microplate in n×m matrix.

2. Description of the Related Art

A microplate liquid handling system has conventionally been known which is used to deliver reagent, specimen, etc. to desired ones of a plurality of wells formed in a microplate. The microplate liquid handling system has a dispensing mechanism and a moving mechanism, and the dispensing mechanism is equipped with a cylinder having a nozzle. Mounted to the nozzle is a dispensing tip, through which liquid can be sucked and discharged. The cylinder is equipped with a plunger for sucking liquid into the dispensing tip mounted to the nozzle and for discharging liquid from the interior of the dispensing tip.

As disclosed, for example, in JP 8-271528 A and JP 5-232124 A, the moving mechanism is capable of moving the nozzle to an appropriate position above a desired well in the microplate, and the dispensing mechanism can be moved in the lateral, longitudinal, and vertical directions (the X-, Y-, and Z-axis directions) above the microplate. Generally speaking, arranged in the microplate are 96 wells in 12×8 matrix, and so-called dispensing is conducted, that is, reagent or specimen is delivered to a desired well from a dispensing tip mounted to the nozzle of the cylinder of the dispensing mechanism, so that reagent-specimen reaction or the like is effected in the well.

There are four types of microplate liquid handling system: 12-gang type, 8-gang type, single-gang type, and 96-gang type. In a 12-gang type microplate liquid handling system, the nozzles of twelve cylinders arranged in parallel and in a straight line in the longitudinal direction of the microplate are operated in synchronism with each other, and it is possible to perform suction or discharge of liquid such as reagent collectively on the dispensing tips mounted to the twelve nozzles. For example, it is possible to simultaneously discharge reagent onto each of the specimens in the plurality of wells arranged longitudinally in a row in the microplate.

Similarly, in an 8-gang type microplate liquid handling system, eight nozzles arranged in parallel and in a straight line in the lateral direction of the microplate are operated in synchronism with each other, and it is possible to perform suction or discharge of liquid such as reagent collectively on the dispensing tips mounted to the eight nozzles. In a 96-gang type microplate liquid handling system, 96 nozzles arranged in 12×8 matrix are operated in synchronism with each other, and it is possible to perform suction or discharge of liquid such as reagent collectively on the dispensing tips mounted to the 96 nozzles and to discharge reagent or the like simultaneously onto all the 96 wells in the microplate. In a single-gang type microplate liquid handling system, a single nozzle is solely operated.

When discharge is to be performed simultaneously on a plurality of wells in the above conventional 12-gang and 8-gang microplate liquid handling systems, there is a limitation in terms of discharging direction. That is, in the case of the 12-gang type microplate liquid handling system, it is only possible to perform simultaneous discharge on a plurality of wells arranged in a row in the longitudinal direction, and it is impossible to perform simultaneous discharge on a plurality of wells arranged in a row in the lateral direction. In the case of the 8-gang type microplate liquid handling system, it is only possible to perform simultaneous discharge on a plurality of wells arranged in a row in the lateral direction, and it is impossible to perform simultaneous discharge on a plurality of wells arranged in a row in the longitudinal direction.

In the case of the 96-gang type microplate liquid handling system, suction and discharge are performed collectively on all the 96 wells in the microplate, so that it is impossible to dispense liquid onto a particular longitudinal row or to perform automatic dispensing on a particular lateral row. That is, after performing dispensing on a longitudinal row, the dispensing tip must be replaced manually before dispensing can be performed on a lateral row. In the case of the single-gang type microplate liquid handling system, it is possible to perform suction or discharge on an arbitrary one of the 96 wells whether it is in the longitudinal or lateral direction of the microplate. However, it is impossible to perform suction/discharge operation simultaneously and collectively on a plurality of wells. Thus, control of time, which is an important factor in drug metabolic reaction, involves a problem. For example, the reaction time differs from well to well.

Thus, none of the above-mentioned conventional microplate liquid handling system is capable of performing a drug metabolic reaction test or the like in which it is necessary to automatically conduct collective suction/discharge operation in both the longitudinal and lateral directions in a single microplate.

SUMMARY OF THE INVENTION

It is therefore an object of the present invention to provide a microplate liquid handling system capable of automatically executing collective suction/discharge operation on particular rows of a microplate in both longitudinal and lateral directions.

This and other objects of the present invention will be attained by a microplate liquid handling system including a main frame body, a dispensing mechanism, a moving mechanism, and a rotation mechanism. The dispensing mechanism includes a plurality of cylinders extending side by side and in parallel with each other to provide a linear cylinder array. Each cylinder has a nozzle and a plunger and each dispensing tip is attachable to each nozzle for performing suction and discharge of liquid reagent or specimen through the dispensing tips by way of each plunger. The moving mechanism is supported to the main frame body for moving the dispensing mechanism in X-axis, Y-axis, and Z-axis directions directed perpendicular to each other. The rotating mechanism rotates the dispensing mechanism by a predetermined angle about a vertically directed rotation axis for changing a direction of the array of the plurality of cylinders.

DETAILED DESCRIPTION OF THE PREFERRED EMBODIMENTS

Figure 1:
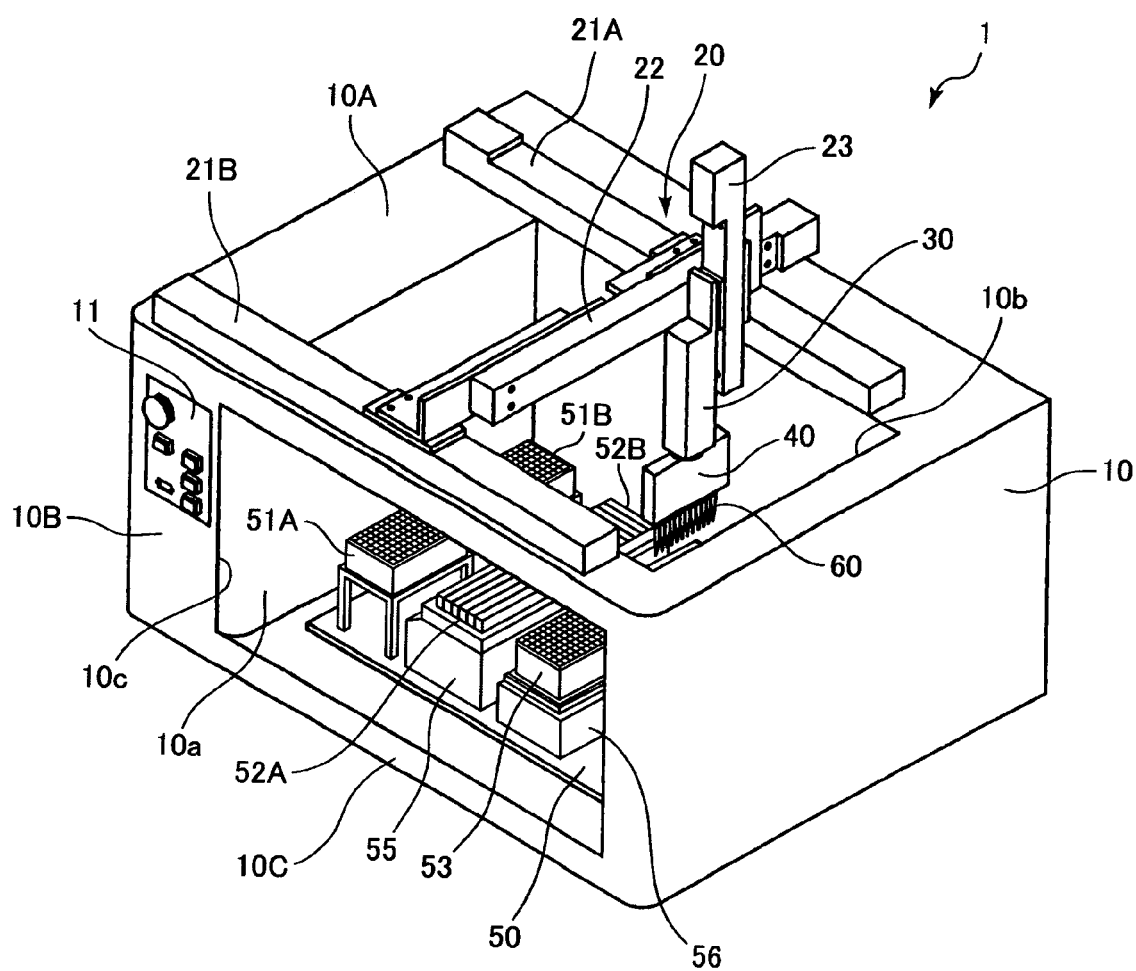
FIG. 1 is a perspective view of a microplate liquid handling system according to a first embodiment of the present invention.

A microplate liquid handling system according to a first embodiment of the present invention will now be described with reference to FIGS. 1 through 5. A microplate liquid handling system 1 has a main body 10, which is equipped with a moving mechanism 20, a rotating mechanism 30, a dispensing mechanism 40, and a stage 50. The main body 10 has a substantially rectangular box-like outward configuration, and defines therein a substantially rectangular chamber 10a which is substantially geometrically similar to the outward configuration of the main body 10. Partially formed in an upper surface 10A and a front surface 10B of the main body 10 are openings 10b and 10c outwardly open from within the chamber 10a. The openings 10b and 10c have rectangular configurations which are respectively substantially geometrically similar to those of the upper surface 10A and the front surface 10B. The stage 50 is provided on an inner peripheral surface defining the chamber 10a, on a bottom surface 10C of the main body 10. Further, the main body 10 is equipped with a switch group 11, a control device (not shown), etc. for effecting, starting, stopping, etc. of the microplate liquid handling system 1. The above-mentioned control device (not shown) controls the movements of the moving mechanism 20 in the X-, Y-, and Z-axis directions described later, rotation of the dispensing mechanism 40, and suction/discharge by dispensing tips 60 attached to nozzles 46. Further, this control device allows arbitrary storage of a test process by an external input device (not shown).

X-axis members 21A and 21B forming the moving mechanism 20 are fixedly provided on the upper sides of the front surface and the rear surface of the main body 10, respectively, The X-axis members 21A and 21B are formed into substantially square pillars, and are immovable with respect to the main body 10. These two X-axis members 21A and 21B extend along the upper sides of the front surface and the rear surface and are parallel to each other. Between the two X-axis members 21A and 21B, there is provided a Y-axis member 22 substantially in the form of a square pillar and extending across the two X-axis members 21A and 21B. The Y-axis member 22 is capable of moving in the longitudinal direction (X-axis direction) of the X-axis members 21A and 21B while being kept perpendicular to the X-axis members 21A and 21B. Further, on the Y-axis member 22 and at a position between the two X-axis members 21A and 21B, there is provided a Z-axis member 23 substantially in the form of a square pillar and extending vertically and perpendicular to the Y-axis member 22. The Z-axis member 23 is capable of moving in the Y-axis direction while being kept perpendicular to the Y-axis member 22. Thus, the X-axis members 21A and 21B allow the Y-axis member 22 to move to the right and left with respect to the main body 10, and the Y-axis member 22 allows the Z-axis member 23 to move forwards and backwards with respect to the main body 10. The Y-axis member 22 and the Z-axis member 23 constitute the moving mechanism 20 together with the X-axis members 21A and 21B.

Figure 2A:
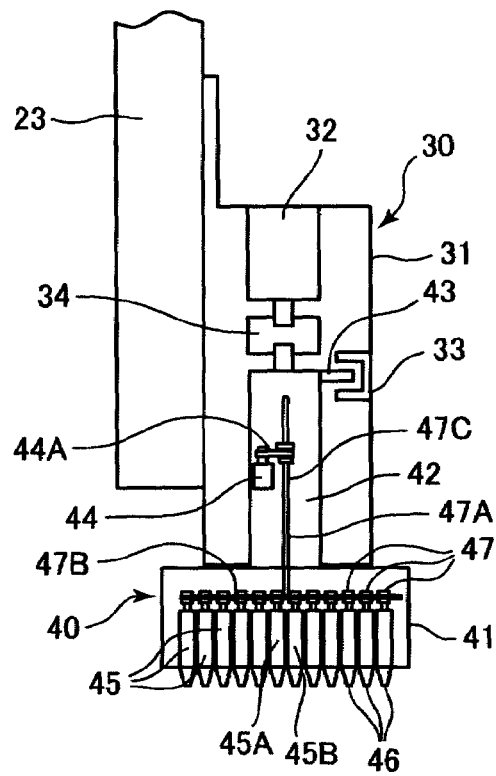
FIG. 2A is a schematic diagram showing a rotating mechanism and a dispensing mechanism in the microplate liquid handling system of the first embodiment of the present invention, and shows a state in which the dispensing mechanism is at the origin.
Figure 2B:
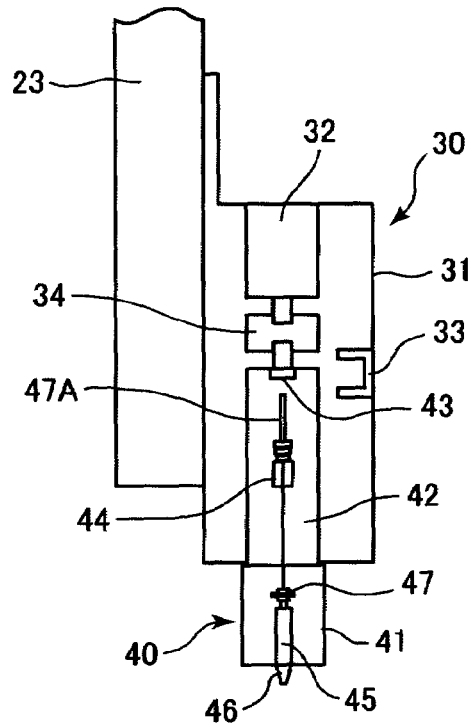
FIG. 2B is a schematic diagram showing a rotating mechanism and a dispensing mechanism in the microplate liquid handling system of the first embodiment, and shows a state in which the dispensing mechanism is at a 90-degrees position.

The rotating mechanism 30 and the dispensing mechanism 40 are connected to the Z-axis member 23. As shown in FIGS. 2A and 2B, the rotating mechanism 30 is equipped with a rotating mechanism main body 31, a stepping motor 32 provided in the main body 31, an origin detection photo sensor 33, and a coupling 34. The rotating mechanism main body 31 is mounted so as to be movable on the Z-axis member 23 in the longitudinal direction of the Z-axis member 23. The stepping motor 32 and the dispensing mechanism 40 are connected through the coupling 34, and the rotation of the stepping motor 32 is transmitted to the dispensing mechanism 40 through the coupling 34. The origin detection photo sensor 33 is firmly attached to the rotating mechanism main body 31, and has a light emitting portion and a light receiving portion (those not shown). An origin position (FIG. 2A) of the dispensing mechanism 40 can be detected when the light receiving portion is shielded by an origin detection dog 43 provided on the dispensing mechanism 40 described later.

The dispensing mechanism 40 is provided at the vertical lower end of the rotating mechanism main body 31, and the dispensing mechanism 40 is supported by the Z-axis member 23 through the intermediation of the rotating mechanism 30. Thus, the Z-axis member 23 is capable of vertically moving the dispensing mechanism 40 through the rotating mechanism 30, with the result that the dispensing mechanism 40 is movable by the moving mechanism 20 in the directions of the X-axis members 21A and 21B, the Y-axis member 22, and the Z-axis member 23, that is, up and down, to the right and left, and forward and backwards with respect to the main body 10.

The dispensing mechanism 40 is composed of a cylinder retaining portion 41 and a supported portion 42. The supported portion 42 is substantially in the form of a cylinder, the longitudinal direction of which is parallel to the Z-axis direction (vertical direction). The upper vertical end of the supported portion 42 is detachably connected to the coupling 34 of the rotating mechanism 30, and the rotation of the stepping motor 32 is transmitted to the supported portion 42 through the coupling 34, rotating the supported portion 42 about a vertically directed rotation axis. Since the upper vertical end of the supported portion 42 is detachable with respect to the coupling 34 of the rotating mechanism 30, the dispensing mechanism 40 is detachable with respect to the rotating mechanism 30. Thus, when the cylinder, nozzles, etc. are damaged, the operation of the microplate liquid handling system can be resumed quickly by replacing the dispensing mechanism portion alone. The origin detection dog 43 protrudes horizontally from the upper vertical end of the supported portion 42, making it possible, as stated above, to detect the origin position of the dispensing mechanism 40 is at the origin position, which will be described below.

Further, a motor 44 for vertically operating a plunger 47 described later is provided inside the supported portion 42.

The cylinder retaining portion 41 is provided at the lower vertical end of the supported portion 42. The cylinder retaining portion 41 is rotatable integrally with the supported portion 42. Thus, the dispensing mechanism 40, which is composed of the cylinder retaining portion 41 and the supported portion 42, is rotatable about a vertically directed rotation axis. The cylinder retaining portion 41 is equipped with twelve cylinders 45. The twelve cylinders 45 are of the same cylindrical configuration, and, as shown in FIGS. 1, 2A and 2B, their axes are vertically directed, provided at equal intervals and parallel to each other, and linearly arrayed in a horizontal row.

The position of the midpoint of the length of the array of twelve cylinders 45, that is, the position between the sixth and seventh cylinders 45A and 45B, as counted from one end of the array, coincides with the position of the rotation axis of the dispensing mechanism 40. As shown in FIG. 2A, the rotating position of the dispensing mechanism 40 at which the cylinders 45 are arrayed in a direction in parallel with the Y-axis member 22, is referred to as the origin position of the dispensing mechanism 40, and this direction is referred to as the origin direction. Further, as shown in FIG. 2B, the rotating position of the dispensing mechanism 40 at which the cylinders 45 are arrayed in a direction perpendicular to the Y-axis member 22 is referred to as the 90-degrees position of the dispensing mechanism 40, and this direction is referred to as the 90-degrees direction.

Since the rotation axis is at the center of the row of the plurality of cylinders 45 arrayed linearly, movement of the dispensing mechanism 40 by the moving mechanism 20 and positioning of the dispensing mechanism 40 vertically above a desired wells can be performed with reference to the rotation axis, facilitating each dispensing tip to face each target well. Further, the number of cylinders 45 is twelve. This number is in conformity with the longitudinal number of wells of an ordinarily available microplate having 12×8 wells, i.e., ninety-six wells in total.

The nozzles 46 are provided at the lower ends of the cylinders 45. The nozzles 46 have discharge holes which are open directly downwards. In the state in which the dispensing tips 60 (FIG. 5) described later have been mounted to the lower ends of the nozzles 46, air in the dispensing tips 60 is sucked or discharged into the nozzles 46 through the discharge holes, whereby reagent or the like can be sucked into or discharged from the dispensing tips 60. A plunger 47 is provided at the upper end of each cylinder 45. All the plungers 47 are supported by a plunger support member 47A. The plunger support member 47A has an inverted-T-shaped configuration, the horizontal portion 47B of which is connected to all the plungers 47 and the vertical portion 47C of which extends into the supported portion 42. The vertical portion 47C has a spiral teeth which is in meshing engagement with a gear 44A which is drive-connected to the motor 44 provided in the supported portion 42. Thus, by driving the motor 44, the plungers 47 can move vertically, and through this vertical movement, the air in the dispensing tips 60 is sucked or discharged into the cylinders 45 through the discharge holes, whereby liquid can be sucked into the interiors of the dispensing tips 60 mounted to the nozzles 46, or liquid inside the dispensing tips 60 can be discharged therefrom.

The dispensing tips 60, mounted to the forward ends of the nozzles 46, will now be described. The dispensing tips 60, which are well-known in the art, are substantially in the form of tapered short pipes having a larger diameter open end and a smaller diameter open end. One dispensing tip is mounted to one nozzle such that the forward end of the nozzle 46 is covered with the larger diameter opening. Since the dispensing tips 60 are tapered, the tapered portions are brought into press contact with the nozzles 46 when the dispensing tips 60 are fitted onto the nozzles 46, whereby the dispensing tips 60 are retained by the nozzles 46. More specifically, in the state in which they have not been mounted to the nozzles 46 yet, the dispensing tips 60 are contained in a dispensing tip container, with the larger diameter opening being directed vertically upwards. The nozzles 46 are brought above the dispensing tips 60 by the X-axis members 21A and 21B and the Y-axis member 22 of the moving mechanism 20, and are moved vertically downwards by the Z-axis member 23. Thus, the larger diameter opening of the dispensing tip 60 gradually covers the nozzles 46, and the nozzles 46 are covered by the dispensing tips 60 until the tapered portions of the dispensing tips 60 are brought into press contact with the nozzles 46 to thereby mount the dispensing tips 60 to the nozzles 46.

In the state in which the dispensing tips 60 have been mounted to the nozzles 46, the nozzles 46 exhibit larger longitudinal length. When the nozzles 46 are vertically lowered through operation of the Z-axis member 23 to place the nozzles at lower position, the dispensing tips 60 can reach the surface of liquid reagent that has been existing vertically below the nozzles 46. In contrast, in the state in which no dispensing tips 60 are mounted to the nozzles, the nozzles 46 exhibit an accordingly smaller longitudinal length, so that even if the nozzles 46 are brought to the vertically lowermost position through operation of the Z-axis member 23, the forward ends of the nozzles 46 cannot reach the liquid surface. In this way, only the selected nozzles (equipped with the dispensing tips) can reach the liquid surface. Thus, when the dispensing tips 60 are mounted to the nozzles 46 of all the twelve cylinders 45, it is possible to suck/discharge liquid reagent collectively through the entire row of dispensing tips 60 mounted to all the nozzles 46 of the twelve cylinders 45. As stated above, in the suction/discharge process, the liquid reagent is sucked into the dispensing tips 60. Thus, there is no fear of the reagent coming into contact with the nozzles 46 or the cylinders 45. Thus, even when dispensing is performed several times with a plurality of kinds of reagent, there is no need to clean the cylinders 45 and the nozzles 46, and it is only necessary to replace the dispensing tips 60 with new dispensing tips 60.

Figure 5:
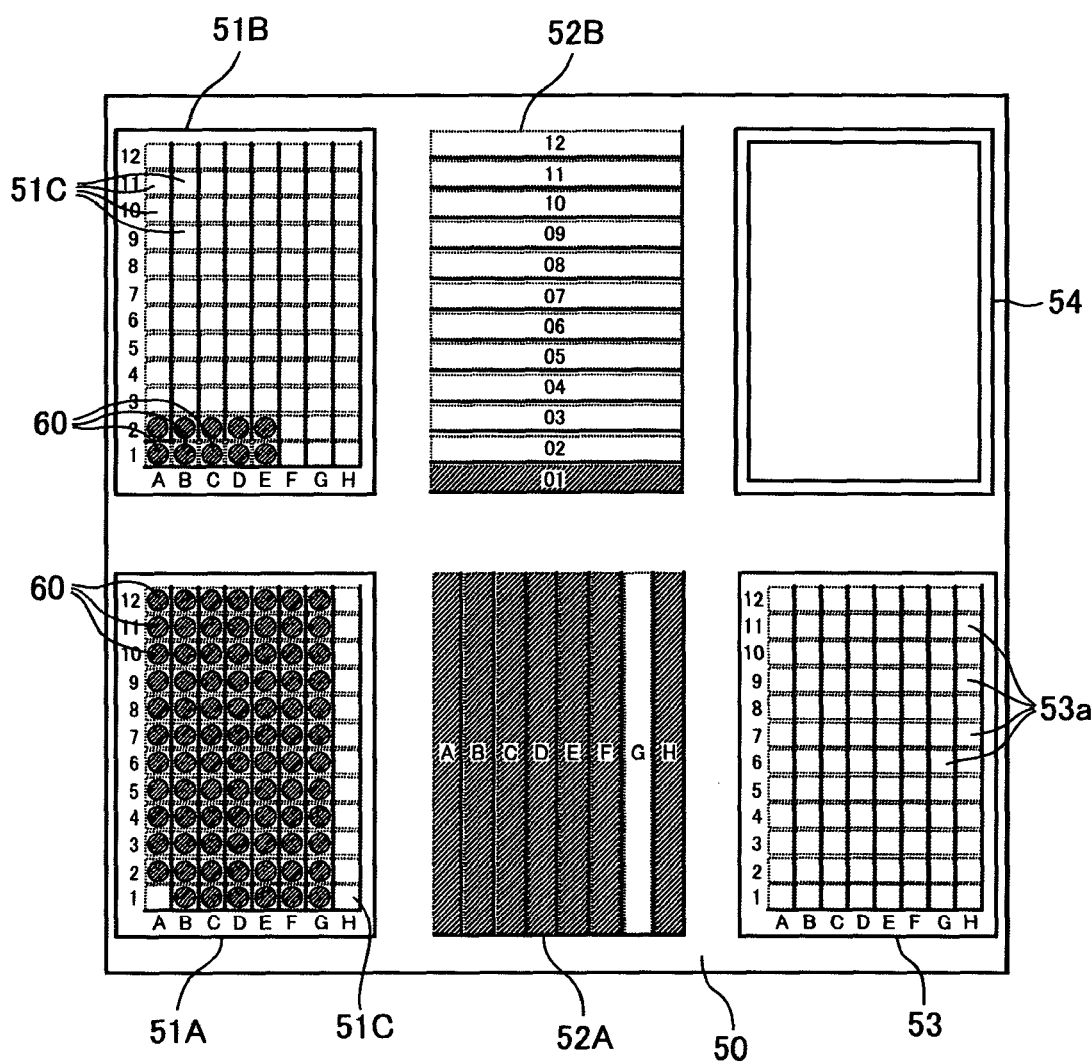
FIG. 5 is a plan view showing the on-stage layout of the microplate liquid handling system of the first embodiment of the present invention.

As shown in FIGS. 1 and 5, arranged on the stage 50 of the main body 10 are first and second dispensing tip containers 51A and 51B containing dispensing tips 60 which are to be attached to the nozzles 46 of the dispensing mechanism 40, a microplate 53 formed in a rectangular outer configuration with 12×8 wells 53a, i.e., 96 in total, arranged in matrix, first and second reagent vessels 52A and 52B containing liquid reagent to be dispensed to the plurality of wells 53a in the microplate 53, and a dispensing tip disposal container 54 for temporarily containing used dispensing tips 60. The first and second dispensing tip containers 51A and 51B are collectively referred to as the dispensing tip containers, and the first and second reagent vessels 52A and 52B are collectively referred to as the reagent vessels.

The microplate 53, the first and second dispensing tip containers 51A and 51B, the first and second reagent vessels 52A and 52B, and the dispensing tip disposal container 54 have substantially the same, rectangular outer configuration. Further, on the stage 50, the microplate 53 is arranged on the front, right-hand side, the first reagent vessel 52A is arranged on the front, middle side, the first dispensing tip container 51A is arranged on the front, left-hand side, the dispensing tip disposal container 54 is arranged on the right-hand, depth side, the second reagent vessel 52B is arranged on the middle, depth side, and the second dispensing tip container 51B is arranged on the left-hand, depth side. The components arranged on the front side and those arranged on the depth side are aligned with their right and left longitudinal sides for orderly arrangement. Similarly, on the front and depth sides, the components arranged on the front and depth sides, the components arranged on the right-hand, middle, and left-hand sides are aligned with their lateral sides for orderly arrangement. Thus, these components including the microplate 53 are all arranged such that their longitudinal direction is parallel to the origin direction.

As shown in FIG. 1, on the stage 50, the microplate 53, the dispensing tip containers 51A, 51B, the reagent vessels 52A, 52B, and the dispensing tip disposal container 54 are placed on predetermined stands 55 and 56. A cooling device (not shown) is connected to the stand 55 on which the reagent vessels are placed for cooling the stand 55, making it possible to cool the reagent vessels 52A, 52B on the stand 55 and to maintain them at a desired temperature. Thus, the stand 55 constitutes a cooler. Further, the microplate 53 is placed on the stand 56 through the intermediation of an aluminum plate (not shown). In the stand 56, there are provided a vibrating device and a heating device, making it possible to agitate specimen and reagent in the wells 53a of the microplate 53 in a heated state. The stand 56 on which the microplate 53 is placed constitutes a thermomixer.

The first dispensing tip container 51A and the second dispensing tip container 51B are respectively equipped with 12×8, i.e., 96 in total, dispensing tip containing holders 51C so that they can respectively contain 12×8, i.e., 96 in total, dispensing tips 60. The first dispensing tip container 51A serves to contain the dispensing tips 60 to be mounted to the nozzles 46 when the dispensing mechanism 40 is at the origin position. As shown in FIG. 5, a desired number of dispensing tips 60 are contained in a state in which they are arranged in a row in the origin direction.

The second dispensing tip container 51B serves to contain the dispensing tips 60 to be mounted to the nozzles 46 when the dispensing mechanism 40 is at the 90-degrees position. As shown in FIG. 5, a desired number of dispensing tips 60 are contained in a state in which they are arranged in a row in the 90-degrees direction. Thus, with the first dispensing tip container 51A, it is possible to mount dispensing tips 60 to all the twelve nozzles 46 of the dispensing mechanism 40, and it is also possible to mount dispensing tips 60 to arbitrary nozzles 46. With the second dispensing tip container 51B, it is possible to mount dispensing tips 60 to arbitrary ones of the third to the tenth nozzles 46 as counted from one end of the row of twelve nozzles 46, and it is possible to mount up to eight dispensing tips.

The first reagent vessel 52A is evenly divided into eight equal longitudinal sections, each of which serves as a reagent vessel, and it is possible to put different reagents in these sections. The second reagent vessel 52B is evenly divided into twelve equal lateral sections, each of which serves as a reagent vessel, and it is possible to put different reagents in these sections. In the first reagent vessel 52A, when the dispensing mechanism 40 is at the origin position, it is possible to suck one specific kind of reagent simultaneously and collectively with the entire nozzle row through all the dispensing tips 60 mounted to the nozzles 46. In the second reagent vessel 52B, when the dispensing mechanism 40 is at the 90-degrees position, it is possible to suck one specific kind of reagent simultaneously and collectively with the entire nozzle row through all the dispensing tips 60 mounted to the nozzles 46. The dispensing tip disposal container 54 serves as a space in which used dispensing tips 60 are temporarily placed after removal of the dispensing tips 60 from the nozzles 46 before the dispensing tips being disposed of.

As described above, the second dispensing tip container 51B, the second reagent container 52B, and the microplate 53 are of the same outer configuration, and the same lateral length. Further, as shown in FIG. 5, in the second dispensing tip container 51B, there are laterally eight dispensing tip containing holders A through H, and in the microplate 53, there are laterally formed eight wells 53a represented by A through H for coincidence in numbers. Thus, when the dispensing mechanism 40 equipped with the twelve nozzles 46 is at the 90-degrees position, it is possible to prevent dispensing tips 60 from being erroneously mounted in a number in excess of eight, which is the number of laterally arranged wells 53a of the microplate 53. Further, it is possible to prevent reagent from being sucked through dispensing tips 60 in a number in excess of eight, which is the number of the laterally arranged wells 53a of the microplate 53. Thus, it is possible to prevent reagent from being discharged from a dispensing tip 60 to a position on the stage 50 where there is no well 53a.

Further, since the first and second reagent vessels 52A and 52B are respectively divided into eight and twelve sections, it is possible to store a plurality of kinds of reagent in the first and second reagent vessels 52A and 52B. Thus, even in the case in which the dispensing mechanism 40 is operated exclusively at the origin position, or in the case in which the dispensing mechanism 40 is operated exclusively at the 90-degrees position, or in the case in which the dispensing mechanism 40 is operated both at the origin position and the 90-degrees position, it is possible to conduct experiments using various kinds of reagent.

Further, due to the provision of the rotating mechanism 30 rotating the dispensing mechanism 40 about the vertically directed rotation axis, both a longitudinal row of wells 53a and a lateral row of wells 53a can be subjected to automatic dispensing by a single microplate liquid handling system with regard to the 12×8, i.e., 96 in total, wells 53a in the microplate 53 arranged on the stage 50. In performing this dispensing, it is possible to discharge liquid reagent simultaneously and collectively through the entire row of nozzles onto the longitudinal row of wells 53a. Further, it is also possible to discharge liquid reagent collectively and simultaneously through the entire nozzle row onto the lateral row of wells 53a. Further, it is possible to collectively suck liquid reagent from the reagent vessel into the dispensing tips 60 mounted to the plurality of nozzles 46 with regard to the entire row of nozzles. Thus, drug metabolic reaction can be performed easily.

Because of the provision of the first and second dispensing tip containers 51A, 51B, the first and second reagent vessels 52A, 52B, it is possible to contain in a classified manner the dispensing tips 60 to be used when discharging reagent to desired wells 53a arranged in one and the other directions, thereby preventing any mistake between dispensing tips 60 for one direction and those for the other direction when automatically attaching the dispensing tips 60 to the nozzles 46. Further, it is also possible to store in a classified manner liquid reagents to be discharged to desired wells 53a arranged in one and the other directions, making it possible to automatically suck reagent into dispensing tips 60 without involving any mistake between tips for one direction and those for the other direction.

Next, the dispensing operation will be described with reference to a drug metabolic reaction test conducted by the microplate liquid handling system 1 constructed as described above. Here, for convenience of illustration, as shown in FIG. 5, each of the components: the microplate 53, the first dispensing tip container 51A, and the second dispensing tip container 51B, is longitudinally divided into portions 1 through 12 and laterally divided into portions A through H, indicating positions where dispensing tips 60 are received through coordinates, as A1, B3, etc. Further, the sub reagent vessels obtained through division of the first reagent vessel 52A are indicated by symbols A through H, from the left to the right, and the sub reagent vessels obtained through division of the second reagent vessel 52B are indicated by numbers 01 through 12, from the front to the depth side.

First, before performing dispensing, 6 μl of specimen is put in the portions A1 through E1 of the microplate beforehand. Further, as shown in FIG. 5, dispensing tips 60 are received beforehand at positions A2–A12 of the first tip container 51A. Similarly, dispensing tips 60 are also received at positions B1–B12 through G1–G12 of the first tip container 51A. Further, dispensing tips 60 are received at positions A1–E1 and positions A2–E2 of the second tip container. Further, reagent 1 constituting dilute solution A is put in the sub reagent vessel A of the first reagent vessel 52A. The dilute solution implies the solution for diluting the specimen. Similarly, reagents 3 through 7 constituting reaction starting solutions A through E are put in the sub reagent vessels B–F of the first reagent vessel 52A. Further, reagent 8 constituting a reaction stopping solution is put in the sub reagent vessel H of the first reagent vessel 52A. Further, reagent 2 constituting dilute solution B is put in the sub reagent vessel 01 of the second reagent vessel 52B.

Next, dispensing operation is conducted. The dispensing operation will be described with reference to two processes: process 1 in which dispensing is conducted with the dispensing mechanism 40 at the 90-degrees position, and process 2 in which the dispensing mechanism 40 is at the origin position. Note that, in process 1, it is assumed that the dispensing mechanism 40 is at the origin position in the initial state, and in process 2, it is assumed that the dispensing mechanism 40 is at the 90-degrees position in the initial state.

Figure 3:
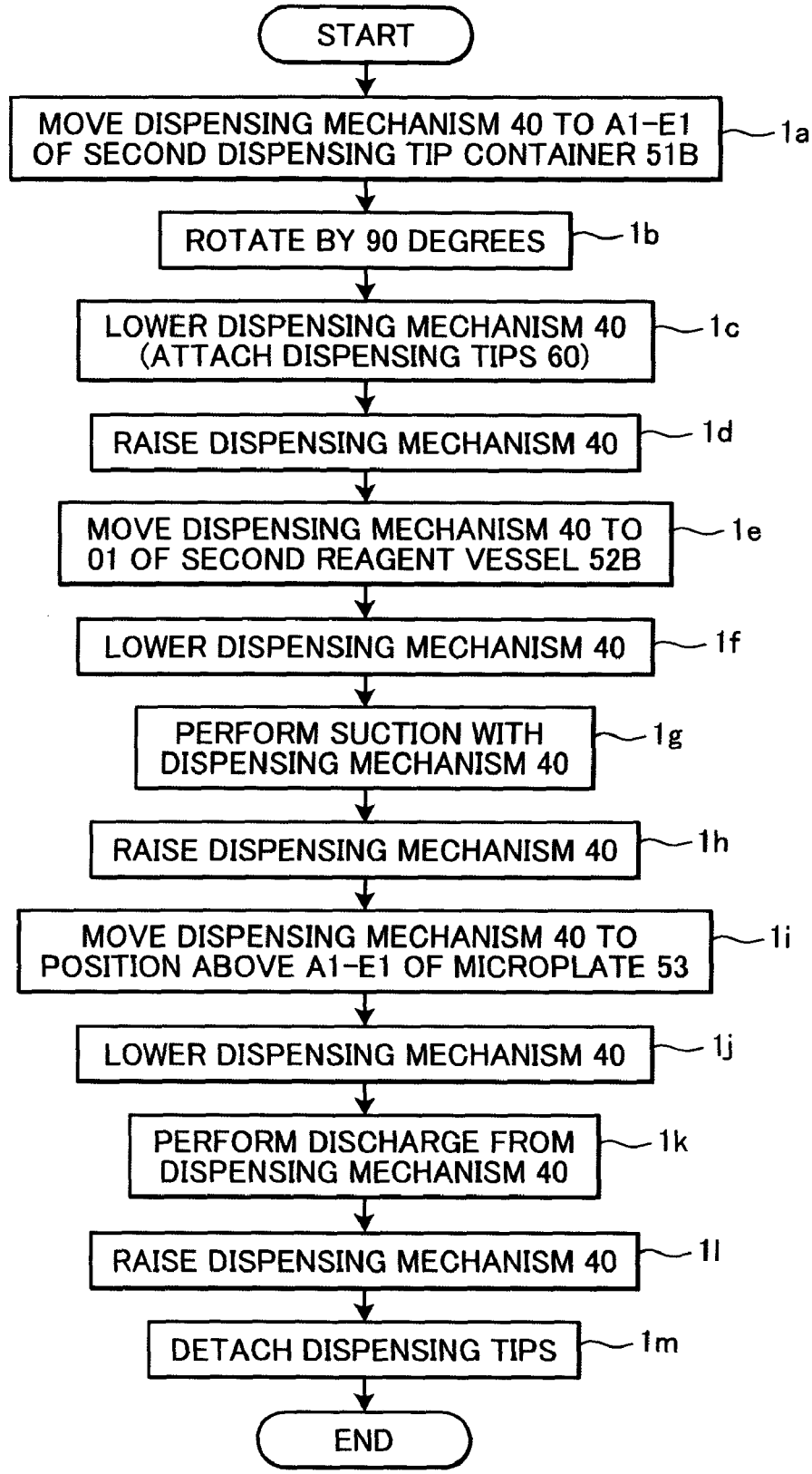
FIG. 3 is a flowchart illustrating dispensing process 1 conducted by the microplate liquid handling system of the first embodiment of the present invention.

As shown in the flowchart of FIG. 3, in process 1, the X-axis members 21A and 21B and the Y-axis member 22 of the moving mechanism 20 are first driven to bring the dispensing mechanism 40 to a position substantially vertically above the portions A1 through E1 of the second dispensing tip container 51B (1a). Next, the rotating mechanism 30 rotates the dispensing mechanism 40 from the origin position to the 90-degrees position to situate the third through seventh nozzles 46, as counted from one end of the row of twelve nozzles 46 of the dispensing mechanism 40 in vertical alignment with the portions A1 through E1 of the second dispensing tip container 51B (1b). Next, the Z-axis member 23 is driven to move the dispensing mechanism 40 vertically downwards to the position where dispensing tips 60 can be attached to the nozzles 46, whereupon the dispensing tips 60 contained in the portions A1 through E1 of the second dispensing tip container 51B are attached to the nozzles 46 of the dispensing mechanism 40 (1c). While in this example the dispensing tips 60 are attached to the third through seventh nozzles 46 as counted from one end of the row of twelve nozzles 46 of the dispensing mechanism 40, this should not be construed restrictively. The dispensing tips may be attached to any positions of the nozzles 46.

Next, the Z-axis member 23 is driven to move the dispensing mechanism 40 vertically upwards (1d). Then, the X-axis members 21A and 21B and the Y-axis member 22 are driven to bring the dispensing mechanism 40 to a position vertically above the portion 01 of the second reagent vessel 52B (1e). Subsequently, the Z-axis member 23 is driven to move the dispensing mechanism 40 vertically downwards until a level (i.e., suction level) is reached at which the smaller diameter forward ends of the dispensing tips 60 attached to the nozzles 46 reach the liquid surface and at which the forward ends of the nozzles 46 with no dispensing tips 60 attached thereto do not reach the liquid surface (1f). Then, 144 μl of reagent 2 constituting dilute solution B is sucked into the dispensing tips 60 (1g).

Next, the Z-axis member 23 is driven to move the dispensing mechanism 40 vertically upwards (1h), and the X-axis members 21A and 21B and the Y-axis member 22 are driven to situate those nozzles 46 of the dispensing mechanism 40 to which the dispensing tips 60 are attached at positions in alignment with the portions A1 through E1 of the microplate 53 (1i). Then, the Z-axis member 23 is driven to move the dispensing mechanism 40 vertically downwards to the reagent discharge position (1j). Then, reagent 2 which has been sucked into the dispensing tips 60 (1g) is discharged to the wells 53a A1 through E1 of the microplate 53 by an amount of 144 μl (1k).

Next, the Z-axis member 23 is driven to move the dispensing mechanism 40 vertically upwards (1l), and the X-axis members 21A and 21B and the Y-axis member 22 are driven to position the dispensing mechanism 40 vertically above the dispensing tip disposal container 54, and the dispensing tips 60 are detached by a dispensing tip detaching mechanism (not shown) (1m) With this, the process 1 is completed.

When rotating the dispensing mechanism 40 from the origin position to the 90-degrees position in step 1b of process 1, a control device (not shown) controls the stepping motor 32. More specifically, the origin position of the dispensing mechanism 40 is set when the origin detection dog 43 shields the light receiving portion (not shown) of the origin detection sensor 33. A control device (not shown) controls the stepping motor 32 such that the dispensing mechanism 40 rotates toward the origin until the origin detection dog 43 shields the light receiving portion (not shown) of the origin detection sensor 33. For rotating the dispensing mechanism 40 from the origin to the 90-degrees position, the control unit drives the stepping motor 32 by the requisite number of pulses for effecting rotation by 90 degrees from the origin position. The dispensing mechanism 40 is rotated by the motor 32, so that, even when the dispensing mechanism 40 is moved to an arbitrary position on the X-axis, Y-axis, and Z-axis by the moving mechanism 20, the dispensing mechanism 40 can be rotated at any arbitrary position.

Figure 4:
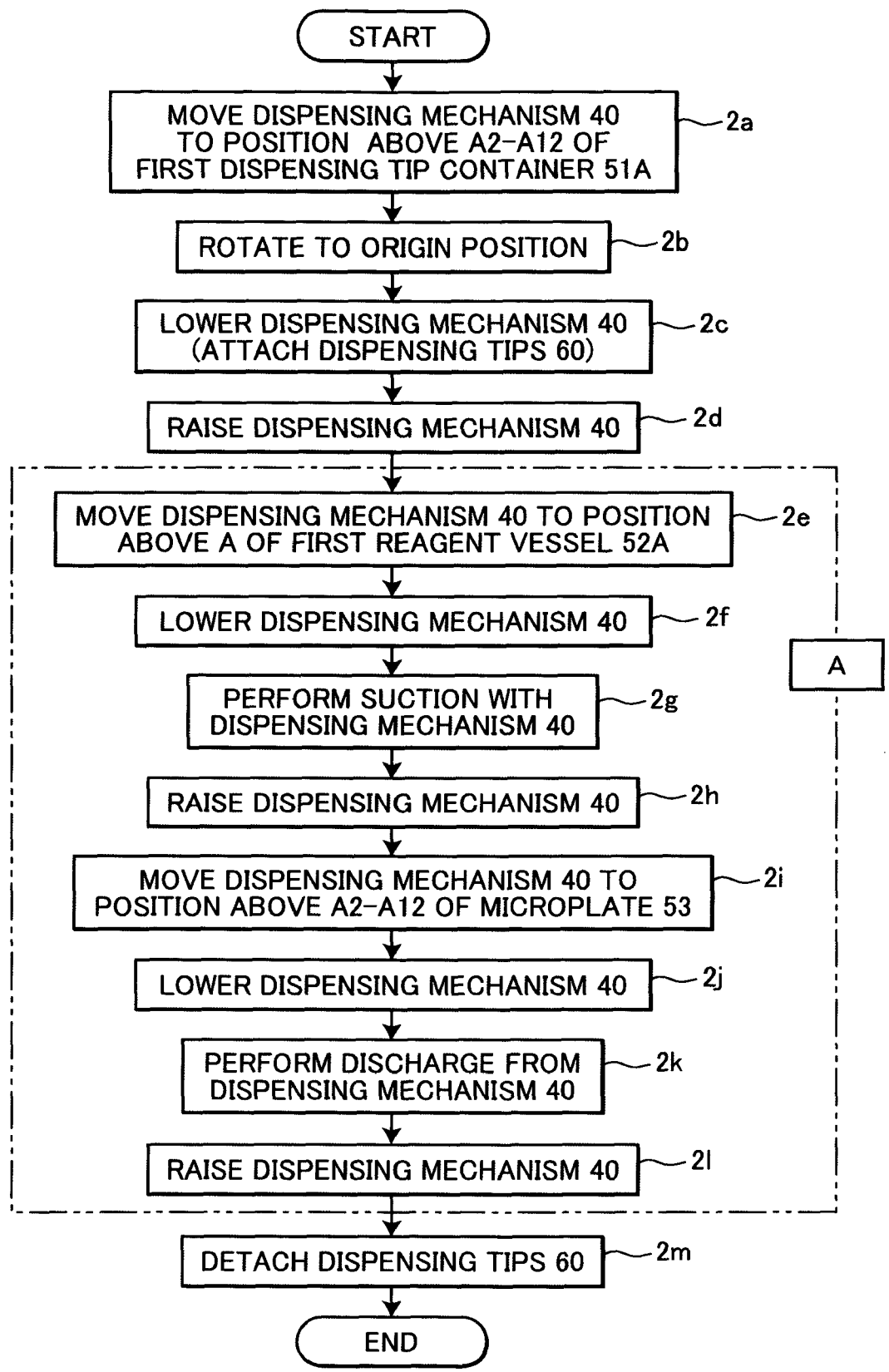
FIG. 4 is a flowchart illustrating dispensing process 2 conducted by the microplate liquid handling system of the first embodiment of the present invention.

Next, as shown in the flowchart of FIG. 4, in process 2, the X-axis members 21A and 21B and the Y-axis member 22 of the moving mechanism 20 are first driven to bring the dispensing mechanism 40 to a position substantially vertically above the portions A2 through A12 of the first dispensing tip container 51A (2a). Next, the rotating mechanism 30 rotates the dispensing mechanism 40 from the 90 degrees position to the origin position to situate all the nozzles 46, except the nozzle 46 of one end of the row of twelve nozzles 46 of the dispensing mechanism 40, in vertical alignment with the portions A2 through A12 of the first dispensing tip container 51A (2b). Next, the Z-axis member 23 is driven to move the dispensing mechanism 40 vertically downwards to the position where dispensing tips 60 can be attached to the nozzles 46 of the dispensing mechanism 40 whereupon the dispensing tips 60 contained in the portions A2 through A12 of the first dispensing tip container 51A are attached to the nozzles 46, except the nozzle 46 of one end of the row of twelve nozzles 46 of the dispensing mechanism 40 (2c).

Next, the Z-axis member 23 is driven to move the dispensing mechanism 40 vertically upwards (2d). Then, the X-axis members 21A and 21B and the Y-axis member 22 are driven to bring the dispensing mechanism 40 to a position vertically above the section A of the first reagent vessel 52A (2e). Subsequently, the Z-axis member 23 is driven to move the dispensing mechanism 40 vertically downwards to the suction level where the smaller diameter forward ends of the dispensing tips 60 attached to the nozzles 46 reach the liquid surface and the forward ends of the nozzles 46 with no dispensing tips 60 attached thereto do not reach the liquid surface (2f). Then, reagent 1 constituting dilute solution A is sucked into the dispensing tips 60 attached to the nozzles 46 (2g).

Next, the Z-axis member 23 is driven to move the dispensing mechanism 40 vertically upwards (2h), and the X-axis members 21A and 21B and the Y-axis member 22 are driven to situate those nozzles 46 of the dispensing mechanism 40 to which the dispensing tips 60 are attached vertically above the portions A2 through A12 of the microplate 53 (2i). Then, the Z-axis member 23 is driven to move the dispensing mechanism 40 vertically downwards to the reagent discharge position (2j). And, reagent 1 which has been sucked into the dispensing tips 60 is discharged to the wells 53a of the portions A2 through A12 of the microplate 53 (2k). Further, as in the series of steps surrounded in box A of FIG. 4, the reagent 1 is also discharged to portions B2–B12 through portions E2–E12.

Next, the Z-axis member 23 is driven to move the dispensing mechanism 40 vertically upwards, and the X-axis members 21A and 21B and the Y-axis member 22 are driven to position the dispensing mechanism 40 vertically above the dispensing tip disposal container 54, and the dispensing tips 60 are detached by the dispensing tip detaching mechanism (not shown) (2m). With this, the process 2 is completed.

Next, in process 3, similar to the process 1, the dispensing tips 60 contained in the portions A2 through E2 of the second dispensing tip container 51B are attached to the nozzles 46 of the dispensing mechanism 40, and after suction of 50 µl from the wells A1 through E1 of the microplate 53, discharge of the sucked liquid to the portions A2 through E2 of the microplate 53 is effected. After the completion of the discharge, suction of 50 µl is effected from the wells A2 through E2, and discharge to A3 through E3 is effected. This operation is repeated up to the wells A8 through E8, preparing dilute specimen solutions diluted stepwise in the microplate 53. Next, the dispensing tips 60 are detached by the dispensing tip detaching mechanism (not shown) to complete process 3.

Next, in process 4, similar to the series of steps of process 2 shown in FIG. 4, the dispensing tips 60 contained in the portions B1 through B12 of the first dispensing tip container 51A are attached to the nozzles 46 of the dispensing mechanism 40, and 100 µl of reagent 3 constituting reaction starting solution A is sucked from the section B of the reagent vessel 52A, and is discharged to the wells A1 through A12 of the microplate 53. Next, the dispensing tips 60 are detached by the dispensing tip detaching mechanism (not shown). Then, the dispensing tips 60 contained in the portions C1 through C12 of the first dispensing tip container 51A are attached to the nozzles 46, and 100 µl of reagent 4 constituting reaction starting solution B is sucked from the section C of the reagent vessel 52A, and is discharged to the wells B1 through B12 of the microplate 53. Next, the dispensing tips 60 are detached by the dispensing tip detaching mechanism (not shown).

Similarly, reagents 5 through 7 constituting reaction starting solutions C through E are respectively poured into the wells C1–C12, D1–D12, and E1–E12 of the microplate 53, and reaction test is started on each well 53a.

Next, in process 5, the dilute specimen solution mixed with the reaction starting solution in the microplate 53 undergo reaction at a fixed temperature for a fixed period of time.

Next, in process 6, after elapse of a previously set arbitrary period, the dispensing tips 60 contained in the portions G1 through G12 of the first dispensing tip container 51A are attached to the nozzles 46 of the dispensing mechanism 40 as in process 2, and 75 µl of reagent 8 constituting reaction stopping solution is sucked from the section H of the reagent vessel 52A, and is discharged to the wells A1 through A12 of the microplate 53. As in the series of steps enclosed in box A in FIG. 4, reagent 8 is poured successively into wells B1–B12 through E1–E12 to stop reaction in each well 53a.

As described above, in the first embodiment, since the rotating mechanism 30 for rotating the dispensing mechanism 40 abut the rotation axis is provided, automatic liquid dispensing operation can be performed with the single dispensing mechanism 40 with respect to the row of wells extending in the longitudinal direction of the microplate 53 and the row of wells extending in the lateral direction thereof. In the dispensing operation, simultaneous fluid discharge can be performed with the wells linearly arrayed. Further, simultaneous fluid suction into dispensing tips can be performed. Accordingly, drug metabolic reaction test can be easily performed.

Figure 6:
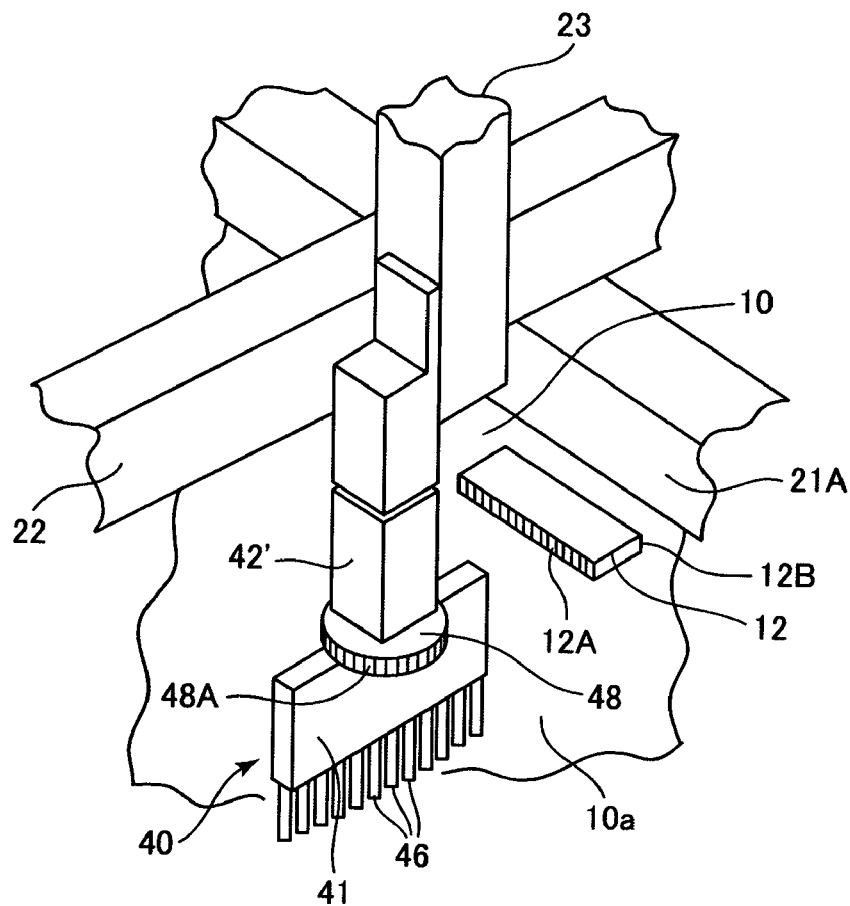
FIG. 6 is a perspective view of an essential portion of a microplate liquid handling system according to a second embodiment of the present invention.

Next, a microplate liquid handling system according to a second embodiment of the present invention will be described with reference to FIGS. 6 and 7. The microplate liquid handling system of the second embodiment only differs from that of the first embodiment in that the rotating mechanism is equipped with a pulley 48 and an abutment member 12 instead of the stepping motor 32. The dispensing mechanism 40 is rotated by the pulley 48 and the abutment member 12.

More specifically, in a portion of the dispensing mechanism 40 and at the position where the cylinder retaining portion 41 and the supported portion 42' are connected, there is provided a disc-shaped pulley 48. The axis of the pulley 48 is in alignment with the rotation axis of the dispensing mechanism 40, and the pulley 48, the cylinder retaining portion 41, and the supported portion 42' are integrally rotatable.

Further, the abutment member 12 in the form of a rectangular plate is provided in the inner peripheral surface which defines the chamber 10a of the main body 10 and which is parallel to the X-axis member 21A. The abutment member 12 is provided in the vicinity of the X-axis member 21A, with its plate-like surface being horizontal, and one long side 12B of the abutment member 12 is firmly attached to the above-mentioned inner peripheral surface. Thus, another longitudinal side 12A of the abutment member 12 is spaced apart from the inner peripheral surface and extends in parallel to the longitudinal direction of the X-axis member.

When rotating the dispensing mechanism 40, the Z-axis member 23 is driven so as to align the vertical height of the pulley 48 with the abutment member 12, and the dispensing mechanism 40 is moved along the X-axis members 21A and 21B so as to confront an outer peripheral surface 48A of the pully 48 with the other longitudinal side 12A of the abutment member 12. Next, the dispensing mechanism 40 is moved along the Y-axis member 22 to bring the outer peripheral surface 48A of the pulley 48 into contact with the other longitudinal side 12A of the abutment member 12. While maintaining this contact state, the dispensing mechanism 40 is moved along the X-axis members 21A and 21B, whereby the pulley 48 receives a force due to the friction between the peripheral surface 48A and the longitudinal side 12A of the abutment member 12, thereby rotating the dispensing mechanism 40.

The control to the rotation angle of the dispensing mechanism 40 is effected by controlling moving amount of the dispensing mechanism 40 along the X-axis members 21A and 21B. Alternatively, the control can be made by detecting the rotation angle by way of an angle sensor provided in the dispensing mechanism 40. Since the dispensing mechanism 40 can be rotated by the pulley 48 and the abutment member 12 instead of the stepping motor 32, a less expensive microplate liquid handing system with a simple construction results.

While the invention has been described in detail and with reference to the specific embodiments thereof, it would be apparent to those skilled in the art that various changes and modifications can be made therein without depart from the scope of the invention. For example, while in the above-described first and second embodiments, the microplate 53 has 12×8 wells 53a, i.e., ninety-six wells in total, this should not be construed restrictively. Generally speaking, the number of wells arranged is a multiple of four in both the longitudinal and lateral directions. For example, it is also possible to double (24 wells) or triple (36 wells) the number of wells arrayed in the longitudinal direction of the microplate.

Further, while in the above embodiments the X-axis members 21A and 21B are immovably fixed to the main body 10, two Y-axis members can be immovably fixed to the main body 10, whereas an X-axis member extends across the two Y-axis members. In the latter case, the X-axis member is movable in the longitudinal direction of the Y-axis members (Y-axis direction) while being maintained at right angles with respect to the Y-axis members.

Further, in the second embodiment the abutment member 12 is provided on the inner peripheral surface defining the chamber 10a inside the main body 10 and extending in parallel to the X-axis member 21A. However, the abutment member can be provided on another inner peripheral surface extending in parallel to the Y-axis member 22.

Figure 7:
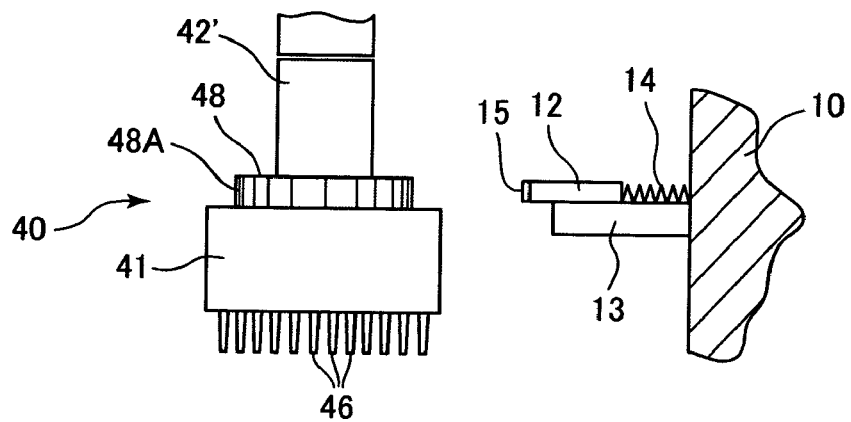
FIG. 7 is a view showing an essential portion of a modification to the second embodiment for description of how an abutment member and a pulley in a microplate liquid handling system of the modification are opposed to each other.

Further, in order to provide constant pressure between the pulley 48 and the abutment member 12, as shown in FIG. 7, a support stand 13 can extend from the main body 10, and the abutment member 12 is supported on the support stand 13. Further, a spring 14 is interposed between the abutment member 12 and the inner peripheral surface of the main body 10, for urging the abutment member 12 toward the pulley 48.

Further, in order to prevent the pulley 48 from slipping with respect to the abutment member 12 during rotation of the dispensing mechanism 40, as shown in FIG. 7, a resilient member 15 formed of a rubber or the like can be laid on the entire longitudinal side 12A of the abutment member 12. This can increase a coefficient of friction between the pulley 48 and the abutment member 12. For a similar purpose, a resilient member can also be formed upon the entire peripheral surface 48A of the pulley 48.

What is claimed is:

1. A microplate liquid handling system comprising:
   a main frame body;
   a dispensing mechanism including a plurality of cylinders extending side by side and in parallel with each other to provide a linear cylinder array, each cylinder having a nozzle and a plunger, and dispensing tips each being attachable to each nozzle for performing suction and discharge of liquid reagent or specimen through the dispensing tips by way of each plunger;
   a moving mechanism supported to the main frame body configured to move the dispensing mechanism in X-axis, Y-axis, and Z-axis directions directed perpendicular to each other; and
   a rotating mechanism that rotates the dispensing mechanism by a predetermined angle about a vertically directed rotation axis for changing a direction of the array of the plurality of cylinders, the rotating mechanism comprising an abutment member fixed to the main frame body, and a disc member disposed coaxially with the rotation axis of the dispensing mechanism and selectively contactable with abutment member, the dispensing mechanism being rotatable about the rotation axis upon movement of the dispensing mechanism by the moving mechanism and upon contact of the disc member with the abutment member.

2. The microplate liquid handling system as claimed in claim 1, wherein the moving mechanism comprises an X-axis member, a Y-axis member, and Z-axis member, extending in the X-axis, Y-axis, and Z-axis directions perpendicular to each other and relatively movable in the X-axis, Y-axis, and Z-axis directions.

3. The microplate liquid handling system as claimed in claim 2, wherein the dispensing mechanism is rotatably supported to the Z-axis member, and
   wherein the abutment member extends in a direction parallel to one of the x-axis and the y-axis, and
   wherein the dispensing mechanism is rotatable about the rotation axis upon movement of the dispensing mechanism in one of the X-axis direction and the Y-axis direction.

4. The microplate liquid handling system as claimed in claim 1, wherein the dispensing mechanism is detachably connectable to the rotating mechanism.

5. The microplate liquid handling system as claimed in claim 1, wherein the dispensing mechanism further comprises a driving unit for moving the plungers up and down.

6. The microplate liquid handling system as claimed in claim 5, wherein the plurality of cylinders have vertical axes extending vertically, and spaced away from each other by an even pitch, and
   wherein each dispensing tip is detachably connected to each nozzle; and
   wherein each nozzle is provided at each lower end of the cylinder and has a discharge hole opened vertically downwards, and
   wherein each plunger is provided at each upper end of the cylinder, suction and discharge of liquid into and from each dispensing tip being effected upon vertical movement of each the plunger.

7. The microplate liquid handling system as claimed in claim 6, wherein the rotation axis is positioned in coincidence with a longitudinal center of the cylinder array.

8. The microplate liquid handling system as claimed in claim 1, wherein the plurality of cylinders comprise twelve cylinders.

9. The microplate liquid handling system as claimed in claim 1, further comprising a microcapsule plate having a plurality of wells arranged in 12×8 matrix, each dispensing tip discharging a liquid onto each well.

* * * * *